(12) United States Patent
Cheng et al.

(10) Patent No.: US 9,642,723 B2
(45) Date of Patent: May 9, 2017

(54) SPINAL IMPLANTS AND INSERTION INSTRUMENTS

(71) Applicant: Alphatec Spine, Inc., Carlsbad, CA (US)

(72) Inventors: Yang Cheng, Foothill Ranch, CA (US); Amardeep Dugal, San Marcos, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 59 days.

(21) Appl. No.: 14/634,073

(22) Filed: Feb. 27, 2015

(65) Prior Publication Data

US 2015/0238327 A1    Aug. 27, 2015

Related U.S. Application Data

(60) Provisional application No. 61/945,314, filed on Feb. 27, 2014, provisional application No. 62/117,384, filed on Feb. 17, 2015.

(51) Int. Cl.
*A61F 2/44*       (2006.01)
*A61F 2/46*       (2006.01)

(52) U.S. Cl.
CPC ............ *A61F 2/4611* (2013.01); *A61F 2/447* (2013.01); *A61F 2002/4623* (2013.01); *A61F 2002/4627* (2013.01); *A61F 2002/4629* (2013.01)

(58) Field of Classification Search
CPC ..................................................... A61F 2/4611
See application file for complete search history.

(56) References Cited

U.S. PATENT DOCUMENTS

| | | | |
|---|---|---|---|
| 5,885,299 A * | 3/1999 | Winslow | A61B 17/861 606/247 |
| 5,928,061 A | 7/1999 | Niino et al. | |
| 7,887,595 B1 | 2/2011 | Pimenta | |
| 8,382,415 B1 * | 2/2013 | Goldbaum | F16B 39/122 411/366.1 |
| 8,702,719 B2 * | 4/2014 | Refai | A61F 2/4611 606/99 |
| 9,284,685 B1 * | 3/2016 | White | D21F 1/486 |
| 2004/0037915 A1 | 2/2004 | Dantlgraber | |
| 2004/0053327 A1 | 3/2004 | Muller | |
| 2004/0210218 A1 | 10/2004 | Dixon et al. | |
| 2005/0141983 A1 | 6/2005 | Fujii et al. | |

(Continued)

*Primary Examiner* — Ellen C. Hammond
*Assistant Examiner* — Stuart S Bray
(74) *Attorney, Agent, or Firm* — Dinsmore & Shohl LLP

(57) ABSTRACT

An instrument for insertion and positioning of a spinal implant includes an outer member, an inner member, and a first thread. The outer member includes a distal attachment feature configured to engage with the spinal implant, a tubular member, and a proximal housing. The inner member is rotatably disposed within a lumen of the outer member and includes a distal coupling feature for coupling with a proximal end of the spinal implant, an elongated shaft within the tubular member, and a proximal end operably coupled with a handle that rotates relative to the proximal housing. The first thread is disposed on the distal coupling feature and includes a first lead and a first thread pitch greater than a thickness of the proximal end of the spinal implant.

17 Claims, 10 Drawing Sheets

(56) References Cited

U.S. PATENT DOCUMENTS

| | | | |
|---|---|---|---|
| 2006/0241770 A1 | * | 10/2006 | Rhoda ................ A61F 2/44 623/17.15 |
| 2008/0287957 A1 | * | 11/2008 | Hester ................ A61B 17/025 606/99 |
| 2009/0210064 A1 | | 8/2009 | Lechmann et al. |
| 2010/0211119 A1 | * | 8/2010 | Refai ................ A61F 2/44 606/86 A |
| 2010/0331897 A1 | * | 12/2010 | Lindner ............ A61B 17/7041 606/305 |
| 2011/0035007 A1 | * | 2/2011 | Patel ................ A61F 2/4465 623/17.11 |
| 2011/0112587 A1 | * | 5/2011 | Patel ................ A61F 2/447 606/86 A |
| 2011/0190892 A1 | | 8/2011 | Kirschman |
| 2013/0023994 A1 | * | 1/2013 | Glerum ............ A61F 2/447 623/17.16 |
| 2013/0060337 A1 | | 3/2013 | Petersheim et al. |
| 2013/0178872 A1 | * | 7/2013 | Shriver ............ A61B 17/0057 606/148 |
| 2013/0238095 A1 | | 9/2013 | Pavento et al. |
| 2013/0345813 A1 | | 12/2013 | Frank et al. |
| 2014/0012380 A1 | | 1/2014 | Laurence et al. |
| 2014/0046447 A1 | | 2/2014 | Dunworth et al. |
| 2014/0277471 A1 | | 9/2014 | Gray et al. |
| 2014/0277497 A1 | | 9/2014 | Bennett et al. |
| 2015/0005879 A1 | | 1/2015 | Georges et al. |
| 2015/0025635 A1 | | 1/2015 | Laubert |
| 2015/0057754 A1 | | 2/2015 | Reed et al. |
| 2015/0238327 A1 | | 8/2015 | Cheng et al. |
| 2015/0328005 A1 | | 11/2015 | Padovani et al. |
| 2015/0328007 A1 | | 11/2015 | Padovani et al. |
| 2015/0328009 A1 | | 11/2015 | Zappacosta et al. |
| 2015/0328010 A1 | | 11/2015 | Martynova et al. |
| 2016/0007983 A1 | | 1/2016 | Frey et al. |
| 2016/0015523 A1 | | 1/2016 | Lewis et al. |
| 2016/0045326 A1 | | 2/2016 | Hansen et al. |
| 2016/0058480 A1 | | 3/2016 | Laubert et al. |
| 2016/0067053 A1 | | 3/2016 | Pisharodi |
| 2016/0166278 A1 | * | 6/2016 | Grant ................ A61B 17/3403 606/86 R |

* cited by examiner

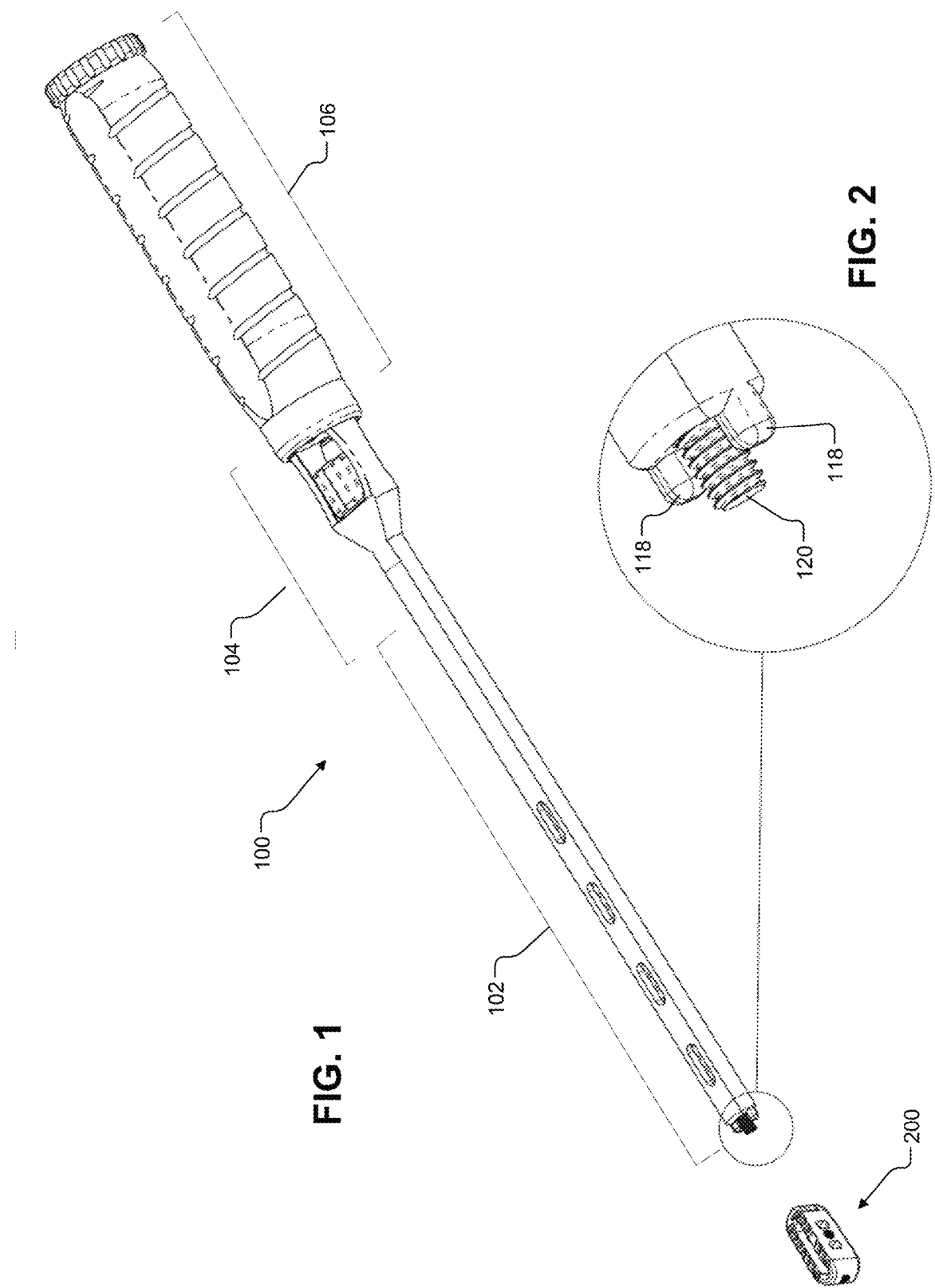

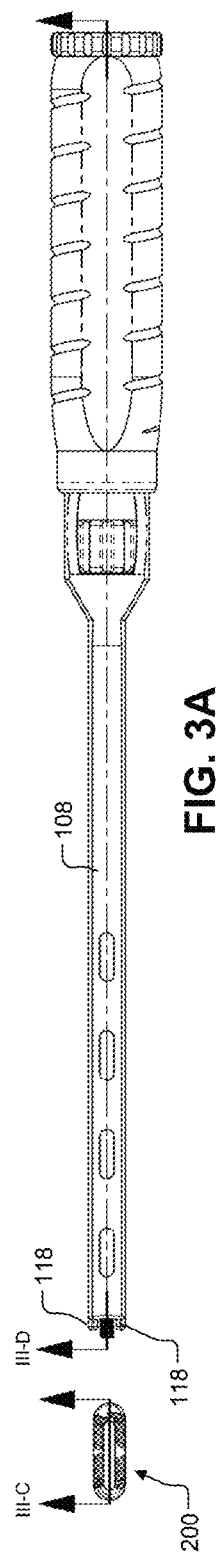
FIG. 3A
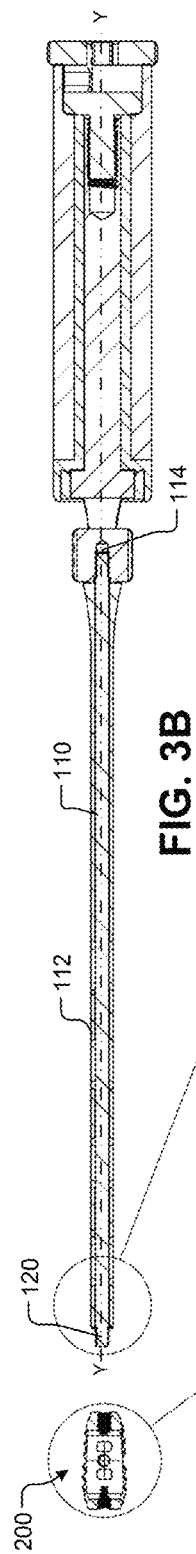
FIG. 3B
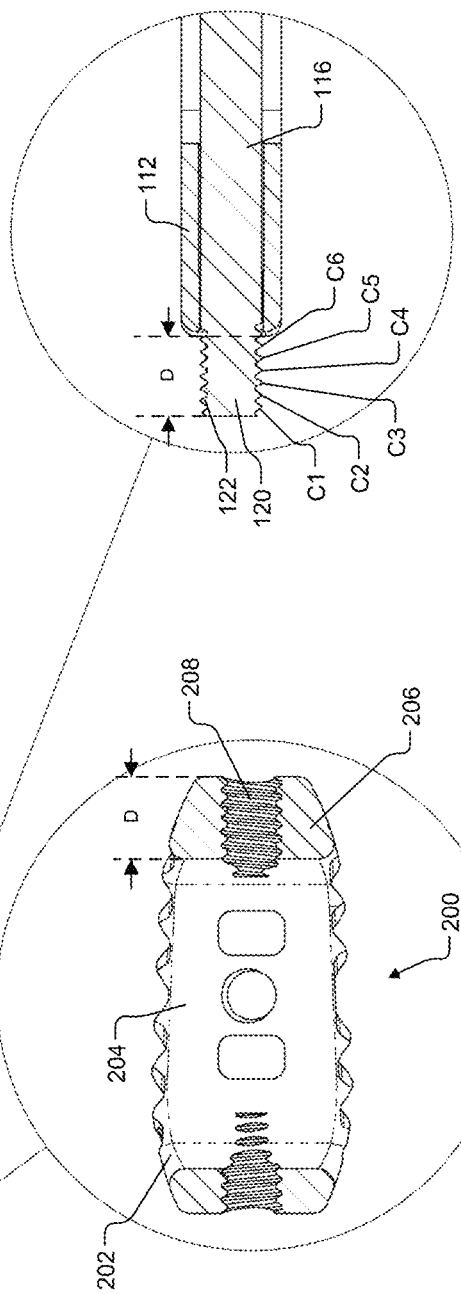
FIG. 3C
FIG. 3D

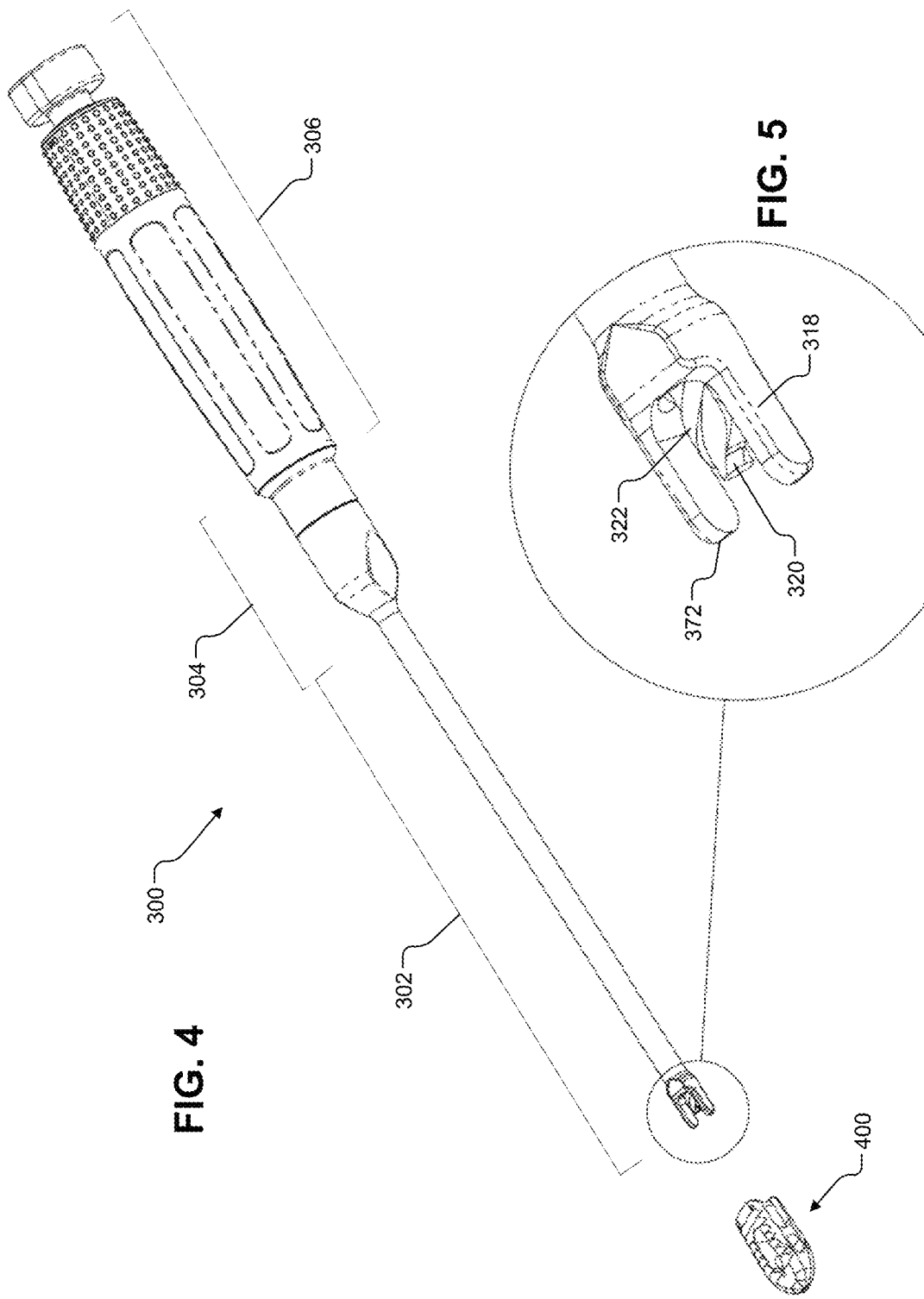

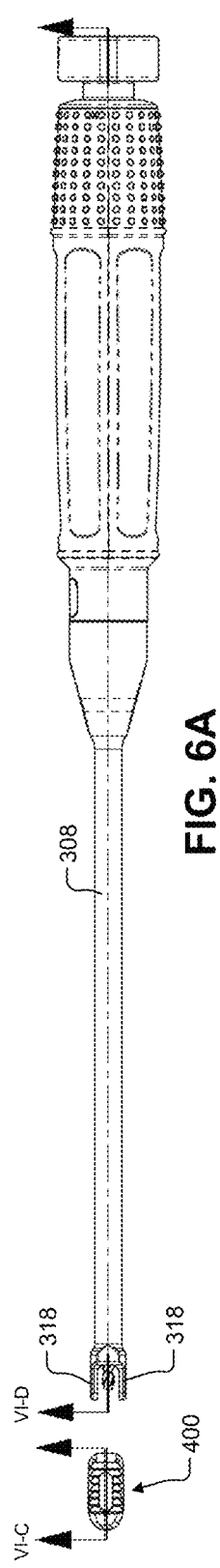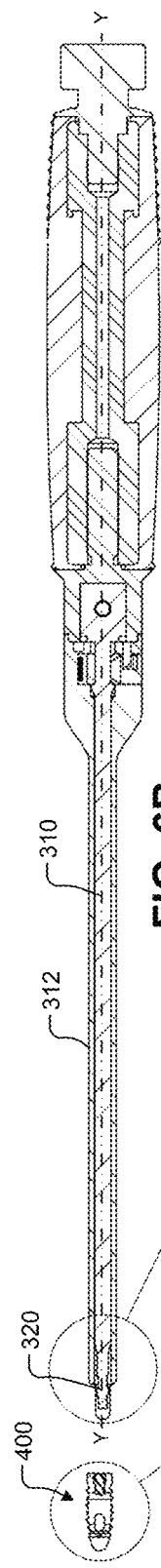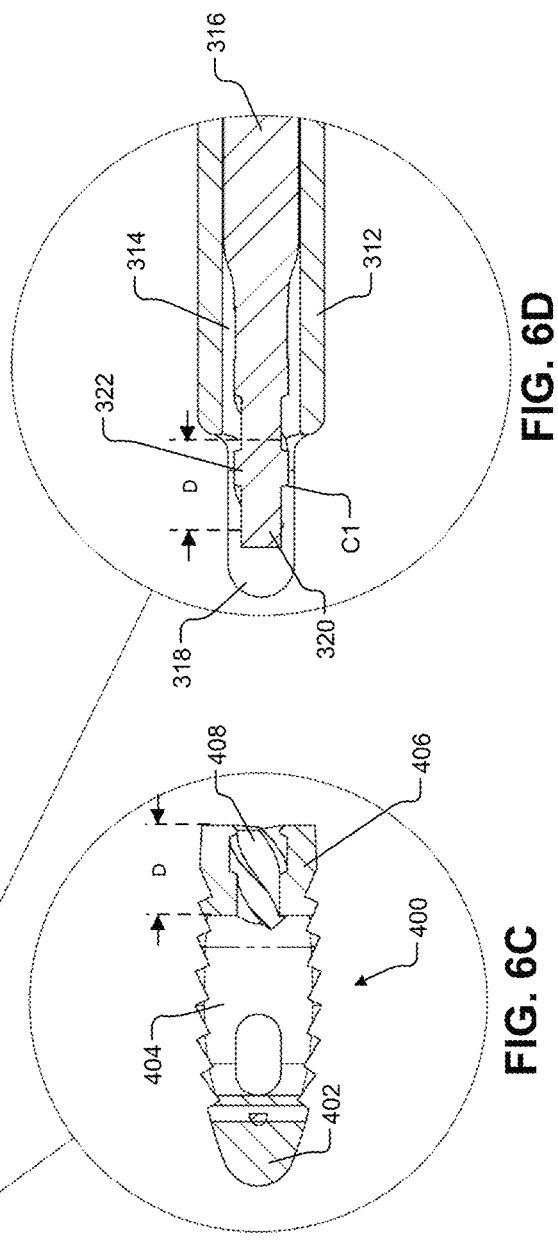

SPINAL IMPLANTS AND INSERTION INSTRUMENTS

CROSS-REFERENCE TO RELATED APPLICATIONS

This application claims priority to U.S. Provisional App. Ser. No. 61/945,314, filed Feb. 27, 2014, and entitled "Systems and Methods for Insertion of Spinal Implants," incorporated by reference in its entirety herein. This application also claims priority to U.S. Provisional App. Ser. No. 62/117,384, filed Feb. 17, 2015, and entitled "Lateral Spacer with Temporary Fixation Plate," incorporated by reference in its entirety herein.

FIELD

The invention generally relates to spinal surgery and more particularly to systems and methods for insertion of spinal implants.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

Patients suffering from orthopedic injuries, deformities, or degenerative diseases often require surgery to stabilize an internal structure, promote healing, and/or relieve pain. In the spinal field, surgeries to correct spinal abnormalities often involve inserting spinal implants such as interbody spacers or cages between adjacent vertebrae to maintain the correct spacing and curvature of the vertebrae. Once the spinal implant has been inserted and maneuvered into proper place, stabilization elements such as screws and rods and/or plates or other types of stabilization elements may be used to secure the spinal implant and vertebrae for proper fusion.

Typically, a lumbar fusion procedure involves insertion of one or more intervertebral spacers through a posterior or transforaminal approach. Posterior lumbar interbody fusion (PLIF) and transforaminal lumbar interbody fusion (TLIF) are fairly common procedures that utilize inserter instruments. For example, U.S. Pat. No. 5,741,253 describes such an inserter. The inserters typically have a coupling feature for coupling with the spinal implant and in some cases, alignment or anti-torque features to prevent rotation of the spinal implant relative to the inserter once coupled with the inserter. The coupling feature may include a threaded fitting that extends into an opening or aperture of the spinal implant. The threaded fitting may be threaded into the opening to secure the spinal implant to the inserter. Additional attachment features may complement features on the spinal implant.

SUMMARY

An instrument for insertion and positioning of a spinal implant includes an outer member, an inner member, and a first thread. The outer member includes a distal attachment feature configured to engage with the spinal implant, a tubular member, and a proximal housing. The inner member is rotatably disposed within a lumen of the outer member and includes a distal coupling feature for coupling with a threaded aperture within the spinal implant, an elongated shaft within the tubular member, and a proximal end operably coupled with a handle to rotate the inner member relative to the outer member. The first thread is on the distal coupling feature and includes a first lead. The first thread includes a first thread pitch greater than or equal to one third of a depth of the threaded aperture of the spinal implant.

In other features, the thread pitch is greater than or equal to the depth of the threaded aperture of the spinal implant. In still other features, the thread pitch is greater than or equal to two times the depth of the threaded aperture of the spinal implant.

In other features, the distal coupling feature includes a second thread with a second lead, the second thread including a second thread pitch equal to the first thread pitch. In still other features, the first thread comprises a long lead trapezoidal form thread.

In other features, one half rotation of the inner member engages less than one full thread of the first thread with the threaded aperture to position the spinal implant into fully coupled engagement with the distal attachment feature. The distal attachment feature comprises a pair of attachment features extending distally in a fork formation around the coupling feature to engage with a pair of recessed portions of the spinal implant.

In other features, the instrument may be combined with the spinal implant. The spinal implant may include a distal end for insertion, a middle section including a pair of recessed portions on an outer surface of the middle section, and a proximal end including the threaded aperture with a thread pitch corresponding to the first thread pitch.

In other features, instrument includes a selector mechanism coupling the proximal end of the inner member with the handle for selectively locking the inner member relative to the outer member. The selector mechanism includes a selector member received by a first recessed portion in a first configuration, a circumferential channel in communication with the first recessed portions in a second configuration, and a second recessed portion in communication with the circumferential channel in a third configuration. When the selector mechanism is in one of the first and the third configurations, the inner member is locked relative to the outer member. When the selector mechanism is in the second configuration, the inner member freely rotates 180 degrees relative to the outer member to secure the spinal implant to the coupling feature and fully engage the distal attachment features with recessed portions of the spinal implant.

An instrument for insertion and positioning of a spinal implant includes an outer member, an inner member, and a selector mechanism. The outer member includes a tubular member, a pair of distal attachment features, and a proximal housing. The inner member includes a distal coupling feature, an elongate shaft, and a proximal end.

The tubular member includes a lumen extending along a longitudinal axis of the tubular member. The pair of distal attachment features includes one of tangs, prongs, and projections that extend distally from the tubular member and are configured to engage with recessed portions of the spinal implant. The proximal housing includes a proximal facing portion with a first recessed portion, a second recessed portion, and a channel communicating between the first and second recessed portions.

The inner member is rotatably disposed within the lumen. The distal coupling feature includes a dual long-lead trapezoidal form thread with a thread pitch greater than a depth of an aperture of the spinal implant. The elongate shaft within the lumen is configured to rotate the distal coupling feature. The proximal end is operably coupled with a handle that rotates the inner member relative to the outer member.

The selector mechanism operably couples the proximal end of the inner member with the handle and includes a selector member with a tab. The tab is positioned within the first recessed portion to prevent rotation of the inner member relative to the outer member in a first configuration. The tab is positioned within the channel while the inner member rotates relative to the outer member to couple the distal coupling feature with the aperture of the spinal implant in a second configuration. The tab is positioned within the second recessed portion to prevent rotation of the inner member relative to the outer member after coupling the spinal implant in a third configuration.

In other features, the first recessed portion and the second recessed portion are arranged at 180 degrees apart on the proximal facing portion of the proximal housing. In other features, the channel comprises a circumferential channel extending 180 degrees on the proximal facing portion of the proximal housing.

In other features, the instrument is combined with the spinal implant. The proximal end of the spinal implant includes an aperture with a mating dual lead Acme thread corresponding to the thread of the distal coupling feature. The pair of recessed portions is disposed on opposite sides of the aperture and extending towards a middle section of the spinal implant.

In still other features, the coupling feature and the spinal implant are in full coupling engagement after one half turn of the handle. Full coupling engagement includes engagement of the distal attachment features with the recessed portions sufficient for insertion and positioning of the spinal implant.

A system for promoting fusion between adjacent vertebrae includes a spinal implant and an instrument for inserting and positioning of the spinal implant. The spinal implant includes a distal end, a middle section, and a proximal end. An aperture in the proximal end includes a dual long-lead trapezoidal form thread. A pair of recessed portions is disposed on opposite sides of the aperture and extends along an outer surface the middle section.

The instrument includes an outer member and an inner member. The outer member includes a tubular member with a lumen extending along a longitudinal axis of the tubular member, a pair of distal attachment features extending distally from the tubular member and configured to engage with the pair of recessed portions, and a proximal housing. The inner member is rotatably disposed within the lumen and includes a distal coupling feature with a mating dual long-lead trapezoidal form thread, an elongated shaft within the lumen configured to rotate the distal coupling feature to couple with the aperture, and a proximal end operably coupled with a handle that rotates the inner member relative to the outer member.

In other features, the instrument of the system further includes a proximal facing portion with a first recessed portion, a second recessed portion, and a channel communicating between the first and second recessed portions. In still other features, a selector mechanism operably couples the proximal end of the inner member with the handle and including a selector member with a tab. The tab is positioned within the first recessed portion to prevent rotation of the inner member relative to the outer member in a first configuration. The tab is positioned within the channel while the inner member rotates relative to the outer member to couple the distal coupling feature with the proximal end of the spinal implant in a second configuration. The tab is positioned within the second recessed portion to prevent rotation of the inner member relative to the outer member after coupling the spinal implant in a third configuration. In still other features, the first recessed portion and the second recessed portion are arranged at 180 degrees about the proximal facing portion of the proximal housing. The open channel includes a circumferential channel extending 180 degrees about the proximal facing portion of the proximal housing.

In other features, the coupling feature and the spinal implant are in full coupling engagement after one half turn of the handle, wherein full coupling engagement includes engagement of the distal attachment features with the recessed portions sufficient for insertion and positioning of the spinal implant.

BRIEF DESCRIPTION OF THE DRAWINGS

FIG. 1 is a perspective view of an exemplary inserter and spinal implant of the prior art.

FIG. 2 is an enlarged view of the distal end of the inserter of FIG. 1

FIG. 3A is side view looking into a superior facing side of the inserter and spinal implant of FIG. 1.

FIG. 3B is a cross-sectional view of the inserter and spinal implant looking into the planes III-C and III-D of FIG. 3A.

FIG. 3C is an enlarged view of the cross-sectional view of the spinal implant looking into the plane III-C of FIG. 3B.

FIG. 3D is an enlarged view of the cross-sectional view of the distal end of the inserter looking into the plane III-D of FIG. 3B.

FIG. 4 is a perspective view of an exemplary inserter and an exemplary spinal implant according to the principles of the present disclosure.

FIG. 5 is an enlarged view of the distal end of the inserter of FIG. 4.

FIG. 6A is side view looking into a superior facing side of the inserter and spinal implant of FIG. 4.

FIG. 6B is a cross-sectional view of the inserter and spinal implant looking into the planes VI-C and VI-D of FIG. 6A.

FIG. 6C is an enlarged view of the cross-sectional view of the spinal implant looking into the plane VI-C of FIG. 6B.

FIG. 6D is an enlarged view of the cross-sectional view of the distal end of the inserter looking into the plane VI-D of FIG. 6B.

DETAILED DESCRIPTION

Figure 7:
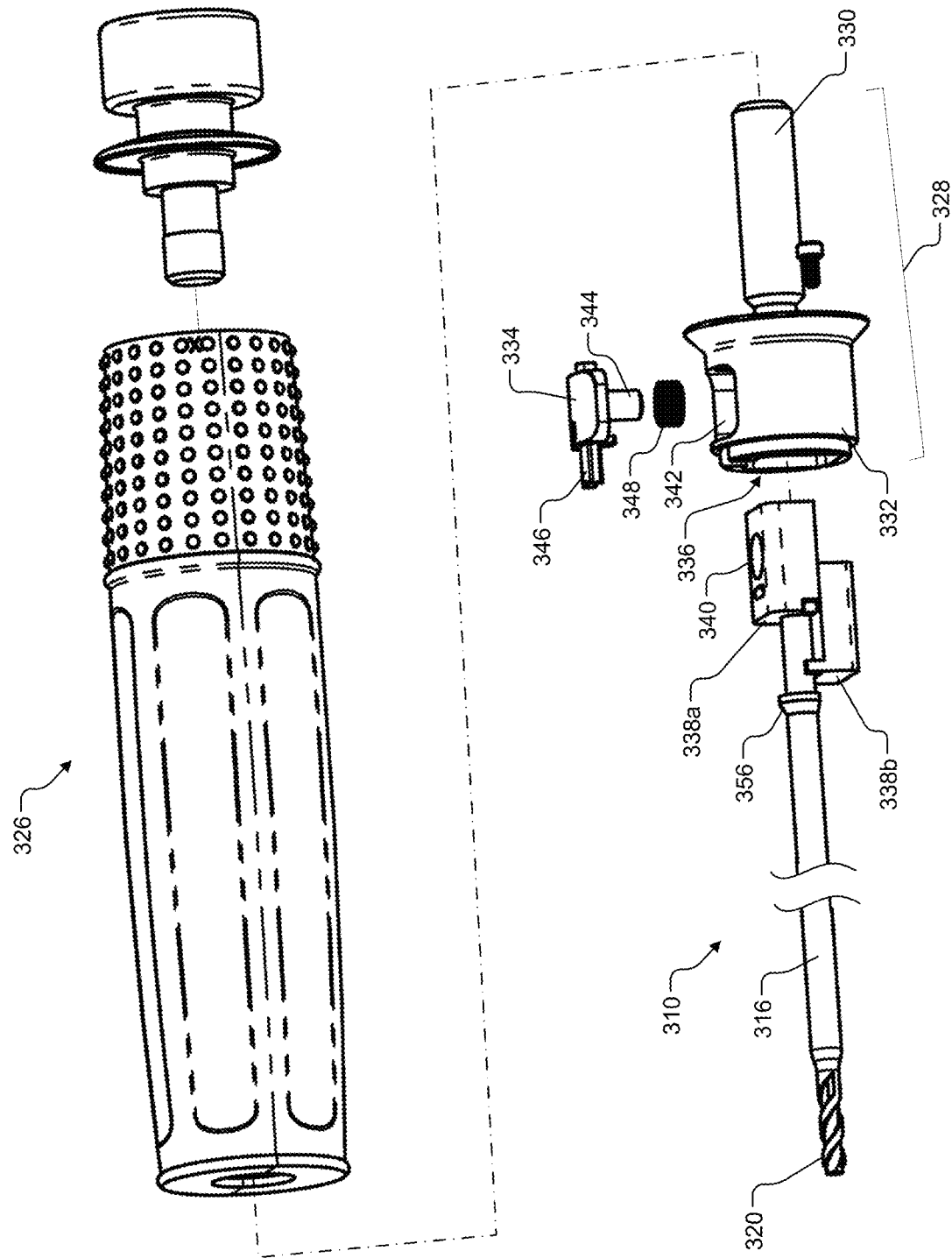
FIG. 7 is an exploded perspective view of an inner member, selector mechanism, and handle of the inserter of FIG. 4.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

In FIG. 1, a typical inserter 100 and spinal implant 200 are illustrated. The inserter 100 includes a distal portion 102, a middle portion 104, and a proximal portion 106. The distal portion 102 may be inserted into a patient during spine surgery and thus includes length sufficient to extend into a surgical site and extend outwardly for manipulation by a surgeon. The middle portion 104 may include one or more control features for coupling the spinal implant 200. The proximal portion 106 may include a handle or gripping portion. The spinal implant 200 may include cages, interbody spacers, and intervertebral implants and may be of various geometries suitable for various surgical approaches including posterior, transforaminal, anterior, lateral, and antero-lateral procedures. FIG. 2 illustrates in greater detail a distal end of the distal portion 102 for coupling with the spinal implant 200.

Referring now also to FIGS. 3A-3D, the distal portion 102 of the inserter 100 may include an outer member 108 for attachment with the spinal implant 200 and an inner member 110 for coupling with the spinal implant 200. For purposes of this disclosure, attachment may include passive attachment such as sliding engagement. Attachment may include the capability to resist rotation of the implant during implant coupling. Coupling may include active coupling such as by threaded coupling. The outer member 108 may include a tubular section 112 having a lumen 114 extending therethrough along a longitudinal axis Y of the inserter 100. The inner member 110 may include an elongated shaft 116 configured to extend through the lumen 114 and rotate therein. At a distal end of the tubular section 112, a pair of attachment features 118 extends distally in a fork formation. The attachment features 118 may be offset from the lumen 114 in a manner to permit the proximal end 206 of the spinal implant 200 to be received therebetween. In some examples, the spinal implant 200 may include depressions, recessed portions, and/or pockets that conform to the shape of the attachment features 118.

At a distal end of the elongated shaft 116, a coupling feature 120 extends distally. The coupling feature 120 may be aligned with the longitudinal axis Y of the inserter 100 in a manner to permit the proximal end 206 of the spinal implant 200 to receive the coupling feature 120. The coupling feature 120 may include a thread 122. The thread 122 may be an external thread. Threads include a thread pitch TP defined as the distance between two adjacent crests of the thread. Most threads are uniform with a constant TP. A larger thread pitch typically indicates a coarse thread with a larger distance between adjacent thread crests. A smaller thread pitch typically indicates a fine thread with a shorter distance between adjacent thread crests.

The thread 122 of a typical inserter may include a thread pitch that is less than a depth D of a threaded aperture 208 of the proximal end 206 of the spinal implant 200. The thread pitch TP is typically less than the depth D by an order of at least 2 times such that at least two crests of the thread 122 engage the spinal implant 200. Typically, the coupling feature 120 permits secure coupling of the spinal implant 200 with the inserter 100 by multiple, full rotations of the inner member 110 to fully engage more than two crests of the thread 122. Multiple crests of the external thread 122 typically must engage with corresponding multiple crests of the internal thread 208 for secure coupling of the spinal implant 200 with the inserter 100. For example, as shown in FIGS. 3C and 3D, the thread 122 includes approximately six crests (C1-C6) to engage with approximately six crests of internal thread 208. Thus, the thread pitch TP is approximately less than or equal to D/6.

These typical inserters and spinal implants, such as inserter 100 and spinal implant 200, often include rotatable inner members with distal coupling features having a relatively fine pitch on the order of D/6. At a minimum, at least one full thread of the inserter 100 should engage the threaded aperture 208 of the spinal implant 200. Typical thread pitches in these inserters 100 are similar to machine screw threads and have a relatively fine thread pitch requiring multiple turns of the inner member 110 to fully couple the spinal implant to the inserter. The rotatable inner member is typically constructed of a metal material such as a stainless steel alloy or a titanium alloy. The spinal implant is typically constructed of either PEEK (polyether ether ketone) or a titanium alloy. Because the materials may differ, cross-threading of either the distal end of the inner member of the inserter or the threaded aperture of the spinal implant may occur.

It is important to quickly and accurately couple the spinal implant to the inserter for many reasons. For example, delays in coupling the spinal implant to the inserter may delay steps in a surgical procedure. Worse, mis-coupling of the spinal implant to the inserter may result in dropped spinal implants that become contaminated and unusable in surgery. Inaccurate coupling of the spinal implant to the inserter may cause poor alignment of the spinal implant within the intervertebral space. Cross-threading of the spinal implant onto the inserter may cause difficulty removing the instrument from the spinal implant after insertion into the patient. Once removed, a cross-threaded spinal implant may be difficult to re-couple with the inserter or other instruments should a revision surgery or other procedure be required. It is also important to have an inserter that is simple to use and simple to clean.

Accordingly, exemplary embodiments of the present disclosure include various features to improve the speed and accuracy of coupling and uncoupling a spinal implant to and from an inserter as well as assembling, disassembling, and cleaning of the inserter. In FIG. 4, an exemplary inserter 300 and spinal implant 400 are illustrated. The inserter 300 includes a distal portion 302, a middle portion 304, and a proximal portion 306. FIG. 5 illustrates in greater detail a distal end of the distal portion 302 for coupling with the spinal implant 400.

The distal portion 302 may be inserted into a patient during spine surgery and thus includes length sufficient to extend into a surgical site and extend outwardly for manipulation by a surgeon. The middle portion 304 may include one or more control features for coupling the spinal implant 400. The proximal portion 306 may include a handle or gripping portion. The spinal implant 40 may include cages, interbody spacers, and intervertebral implants and may be of various geometries suitable for various surgical approaches including posterior, transforaminal, anterior, lateral, and anterolateral procedures.

Referring now also to FIGS. 6A-6D, the distal portion 302 of the inserter 300 may include an outer member 308 for attachment with the spinal implant 400 and an inner member 310 for coupling with the spinal implant 400. For purposes of this disclosure, attachment may include passive attachment such as sliding engagement. Attachment may include the capability to resist rotation of the implant during implant coupling. Coupling may include active coupling such as by threaded coupling. The outer member 308 may include a tubular section 312 having a lumen 314 extending therethrough along a longitudinal axis Y of the inserter 300. The inner member 310 may include an elongated shaft 316 configured to extend through the lumen 314 and rotate therein. At a distal end of the tubular section 312, a pair of attachment features 318 extends distally in a fork formation. The attachment features 318 may be offset from the lumen 314 in a manner to permit the proximal end 406 of the spinal implant 400 to be received therebetween. In some examples, the spinal implant 400 may include depressions, recessed portions, and/or pockets that conform to the shape of the attachment features 318 as illustrated in FIGS. 9A-9B and 10A-10B.

At a distal end of the elongated shaft 316, a coupling feature 320 extends distally. The coupling feature 320 may be aligned with the longitudinal axis Y of the inserter 100 in a manner to permit the proximal end 406 of the spinal implant 400 to receive the coupling feature 320. The coupling feature 320 may include a thread 322. The thread 322 may be an external thread.

Prior coupling features, such as thread 122 described above with reference to inserter 100 included a thread pitch TP typically less than depth D of the threaded aperture 208 by an order of at least three times and typically more on the order of six times such that at least six crests of the thread 122 engage the spinal implant 200. Thus the thread pitch is at least D/3 or more typically on the order of approximately D/6.

The thread 322 of the present inserter 300 may include a thread pitch TP that is greater than prior thread pitches such as thread 122. For example, the thread 322 may include a TP that is greater than one third of depth D of aperture 420 in the proximal end 406 of the spinal implant 400. The thread 322 of the coupling feature 320 permits secure coupling of the spinal implant 200 with the inserter 100 by one half rotation of the inner member 310 to engage less than one full crests of the thread 322. For example, as shown in FIGS. 6C and 6D, the thread 322 includes approximately less than one full thread of engagement, or only one crest C1 to engage with approximately one crest of internal thread of aperture 408. That is, the threaded aperture 408 includes less than one full thread. Thus, the thread pitch TP is greater than or equal to approximately D. For example, the distance to a second crest C2 (not shown) may be greater than the depth D of the threaded aperture 408. For a dual lead thread including a first thread 322-1 and a second thread 322-2, each of the threads 322 may include a thread pitch TP greater than or equal to approximately double the thickness D of the proximal end 406 of the spinal implant 400. Thus, the thread pitch TP of a dual lead thread 322 is approximately greater than or equal to two times D (2×D) or double the depth D of the aperture 408.

In some examples, the coupling feature 320 includes a long lead (pitch) trapezoidal form thread. In some examples, the coupling feature 320 includes a modified Acme thread. In some examples, the 322 thread includes a double lead. In some examples, the thread 322 includes a double lead and a substantially steep thread pitch greater than or equal to approximately two times D where D is a depth of the threaded aperture 408 (or a thickness of the proximal end 406) of the spinal implant 400. In some examples, the coupling feature 320 permits secure coupling of the spinal implant 400 with the inserter 300 by 180 degrees of rotation of the inner member 310 relative to the outer member 308. For example, one half-turn of the inner member 310 may position the coupling feature 320 into full coupling engagement with the threaded aperture 408 in the proximal end 406 of the spinal implant 400. The coupling feature 320 and the spinal implant 400 are in full coupling engagement after one half turn of the handle. Full coupling engagement includes engagement of the distal attachment features 318 with the recessed portions of the spinal implant 400 sufficient for insertion and positioning of the spinal implant 400. Engagement of the distal attachment features 318 with the recessed portions includes engagement of a distal tip of the distal attachment feature 318 with a distal end of the recessed portions.

Figure 8A:
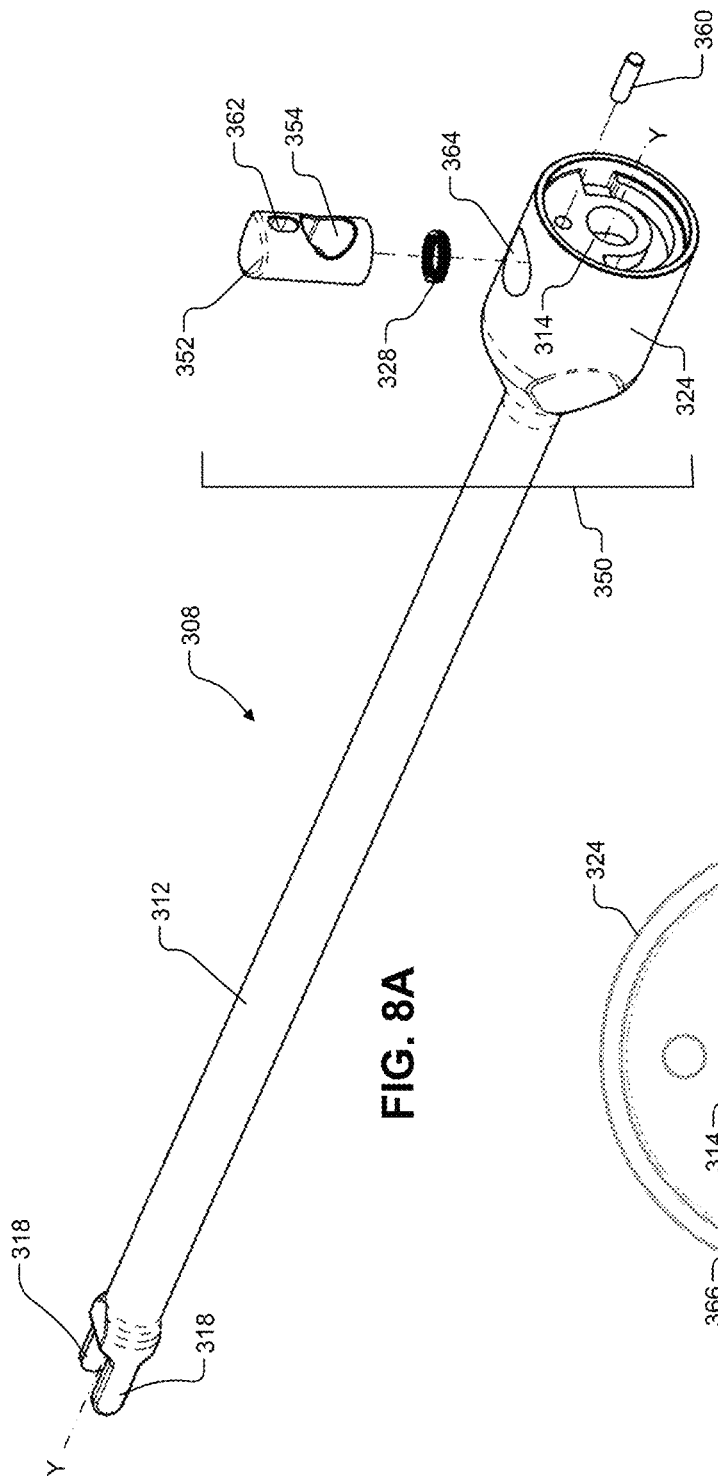
FIG. 8A is an exploded perspective view of an outer member of the inserter of FIG. 4.
Figure 8B:
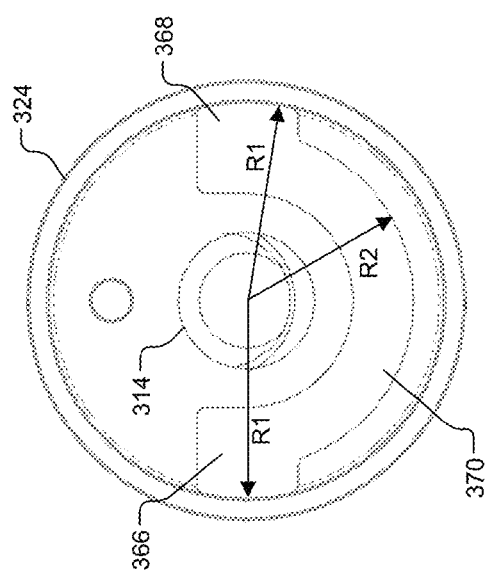
FIG. 8B is a side view looking into a proximal end of the outer member of FIG. 8A.

Referring to FIGS. 8A and 8B, the outer member 308 of the inserter 300 may include a proximal housing 324 extending from a proximal end of the tubular member 312. The proximal housing 324 may be of unitary construction with the tubular member 312 or alternately welded or fitted to the tubular member 312 such that no movement may occur relative to the tubular member 312. The middle portion 304 may include additional features for releasing the outer member 308 and positioning the inner member 310 to couple with the spinal implant 400.

Referring to FIG. 7, the proximal portion 306 of the inserter 300 may include a handle 326 that rotates relative to the outer member 308. The handle 326 may be operably coupled with the inner member 310 to rotate the coupling feature 320. The handle 326 may include grip-enhancing layers, coatings, or other materials for improving the grip of a surgeon. For example, the handle 326 may include silicone grips, depressions, beads, and the like. The handle 326 may include an end cap. The end cap may rotate freely on the proximal end of the handle 326 to permit the user to hold the end cap to stabilize the inserter 300 while rotating the handle 326 to couple the spinal implant 400. The end cap may be used with a hammer or slap-hammer to impact the inserter 300 and force the spinal implant 400 into position between the vertebrae. The handle 326 may include a co-axial handle in line with the longitudinal axis Y of the inserter 300. Alternately, the handle 326 may be offset at some angle relative to the longitudinal axis Y of the inserter 300 to enable a clear view along the axis Y such as for minimally invasive surgical procedures.

Referring now to FIGS. 7 and 8, exploded views of the inserter 300 illustrate additional features for rotating and locking the inner member 310 relative to the outer member 308 and releasing the outer member 308 from the proximal portion 306. At a distal end of the handle 326, a selector mechanism 328 may be fixedly attached to the handle 326 and configured to turn with the handle 326. The selector mechanism 328 may be used to select between at least two inserter configurations. In some examples, the selector mechanism 328 may be used to select between three inserter configurations. For example, the selector mechanism 328 may be used to enable positioning of the inner member 310 in an unlocked configuration and to prevent positioning of the inner member 310 in a locked configuration. In the unlocked configuration, the inner member 310 may be rotatable via the handle 326 relative to the outer member 308. In the locked configuration, the inner member 310 may be rotatably fixed relative to the outer member 308. There may be two different locked configurations and one unlocked configuration.

In some examples, the selector mechanism 328 may include a proximal end 330 coupled with a distal housing 332. The proximal end 330 may be press fit into the handle 326. For example, the proximal end 330 may comprise a metal alloy such as a stainless steel or titanium alloy. The proximal end 330 may include an outer surface having a cross-hatched or knurled texture. The handle 326 may comprise a plastic or rubber material. The proximal end 330 may be heated and pressed into a hollow portion of the handle 326 causing plastic or rubber material inside the handle 326 to melt. The melted material conforms to the outer surface of the proximal end 330 such that the proximal end 330 is secured to the handle 326 to rotate the selector mechanism 328 with the handle 326.

The distal housing 332 may include a cylindrical housing having one or more apertures or openings to receive the inner member 310 and a selector member 334. A proximal end of the distal housing 332 may be fixedly coupled with the proximal end 330 such that together the entire selector mechanism 328 rotates with the handle. The distal housing 332 may include a distal facing opening 336 that receives a proximal end of the shaft 316. The proximal end of the shaft 316 may include receiver 338. The receiver 338 may include one or more portions for ease of assembly and cleaning. For example, the receiver 338 may include a first portion 338a and a second portion 338b. The receiver 338 may receive the selector member 334 in a radially-facing aperture 340.

The distal facing opening 338 may communicate with a radially-facing opening 342 on an outer surface of the housing 332. The selector member 334 may include a radially-facing portion 344 that extends through the radially-facing opening 342 and into the radially-facing aperture 340 of the receiver 338. The selector member 334 further includes one or more tabs 346 extending parallel to the longitudinal axis Y of the inserter 100. The tabs 346 may engage with various portions of the proximal housing 324 of the outer member 108 as described herein to permit the inner member 310 to rotate therein. A bias spring 348 may bias the selector member 334 radially outward.

Continuing now with FIGS. 8A and 8B, the proximal housing 324 may slide over the inner member 310 and couple with the selector mechanism 328. The shaft 316 may freely rotate within the lumen 314 and the distal coupling feature 320 may extend distally from an opening in the lumen between the attachment members 318. The proximal housing 324 may include a release mechanism 350 to release the outer member 308 from the inner member 110 and selector mechanism 328. The release mechanism 350 may include a release member 352 extending radially through an outer surface of the proximal housing 324.

The release member 352 may include a thru-bore 354 that receives the shaft 316. The thru-bore 356 may engage with a flanged portion 356 of the shaft 316 in a first position and may disengage from the flanged portion 356 in a second position to permit the flanged portion 156 to pass through the thru-bore 354. A bias spring 358 may bias the release member 352 radially away from the shaft 316 to engage a portion of the thru-bore 354 with the flanged portion 356 in the first position. A guide pin 360 may extend into a guide slot 362 of the release member 352 to guide the release member 352 towards radial movement relative to the proximal housing 324. The guide pin 360 may prevent the release member 352 from being removed from an aperture 364 in the proximal housing 324.

A distally extending one of the tabs 346 of the selector member 334 may extend into one or more recessed portions of the proximal housing 324 to enable rotation of the inner member 310 as the selector member 334 is depressed radially inward and to prevent rotation of the inner member 310 as the selector member 334 is biased radially outward. For example, as shown in FIG. 8B, the proximal housing 324 may include a proximally facing portion having a first recessed portion 366, a second recessed portion 368, and a circumferential channel 370 extending therebetween. The first recessed portion 366 and the second recessed portion 368 may include an outer radius R1 measured from the longitudinal axis Y of the inserter 300 that is greater than an outer radius R2 of the circumferential channel 370. Thus, when looking into the proximal facing portion of the proximal housing 324, the circumferential channel 370 forms generally a half-circle or U-shape while the first recessed portion 366 and second recessed portion 368 form tabs extending radially away from the ends of the channel 370.

In function, the selector member 334 may be biased into a locking position by the bias spring 348 when the tab 346 is aligned with either of the first or second recessed portion 366 and 368. The tab 346 may be received within the recessed portion. When the selector member 334 is depressed, the tab 346 may be rotated into the circumferential channel 370. The tab 346 may slide within the circumferential channel 370 as the selector mechanism 328 is rotated with the handle 326. The inner member 310, which is coupled with the selector member 334 via radially-facing portion 344, may rotate with the handle 326 and selector mechanism 328.

The selector mechanism 328 couples the proximal end of the inner member 310 with the handle 326 and the selector member 334 positions the tab 346. The tab 346 is positioned within the first recessed portion 366 to prevent rotation of the inner member 310 relative to the outer member 308 in a first configuration. The tab 346 is positioned within the channel 370 while the inner member 310 rotates relative to the outer member 308 to couple the distal coupling feature 320 with the proximal end of the spinal implant 400 in a second configuration. The tab 346 is positioned within the second recessed portion 368 to prevent rotation of the inner member 310 relative to the outer member 308 after coupling the spinal implant 400 in a third configuration. The first recessed portion 366 and the second recessed portion 368 may be arranged at 180 degrees apart about the proximal facing portion of the proximal housing 324. The channel 370 may include a circumferential channel extending 180 degrees about the proximal facing portion of the proximal housing 324 and in communication with the first recessed portion 366 and the second recessed portion 368. The coupling feature 320 and the spinal implant 400 are in full coupling engagement after one half turn of the handle 326. Full coupling engagement includes engagement of the distal attachment features 318 with the recessed portions of the spinal implant 400 sufficient for insertion and positioning of the spinal implant 400.

Figure 9A:
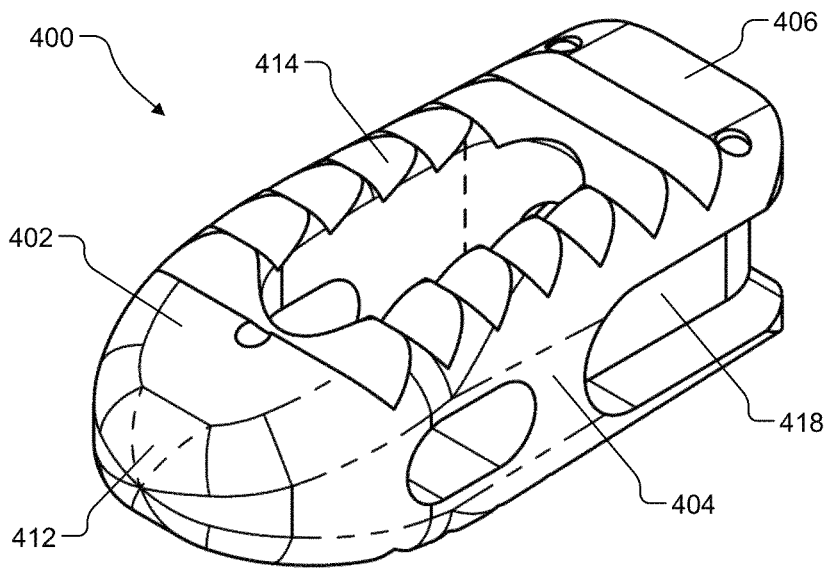
FIGS. 9A and 9B are perspective views of the exemplary spinal implant of FIG. 4 according to the principles of the present disclosure.
Figure 9B:
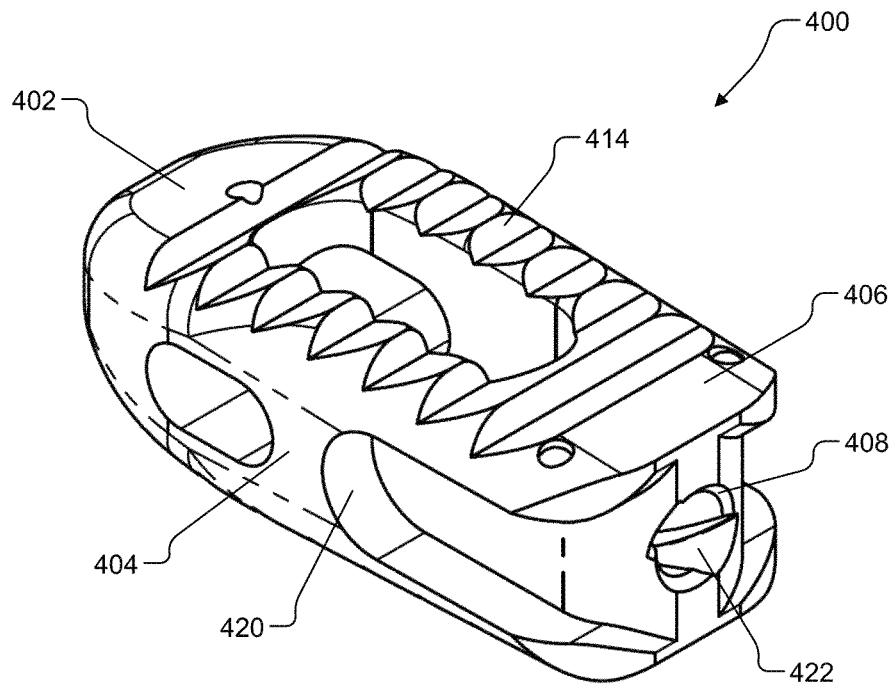
Figure 9C:
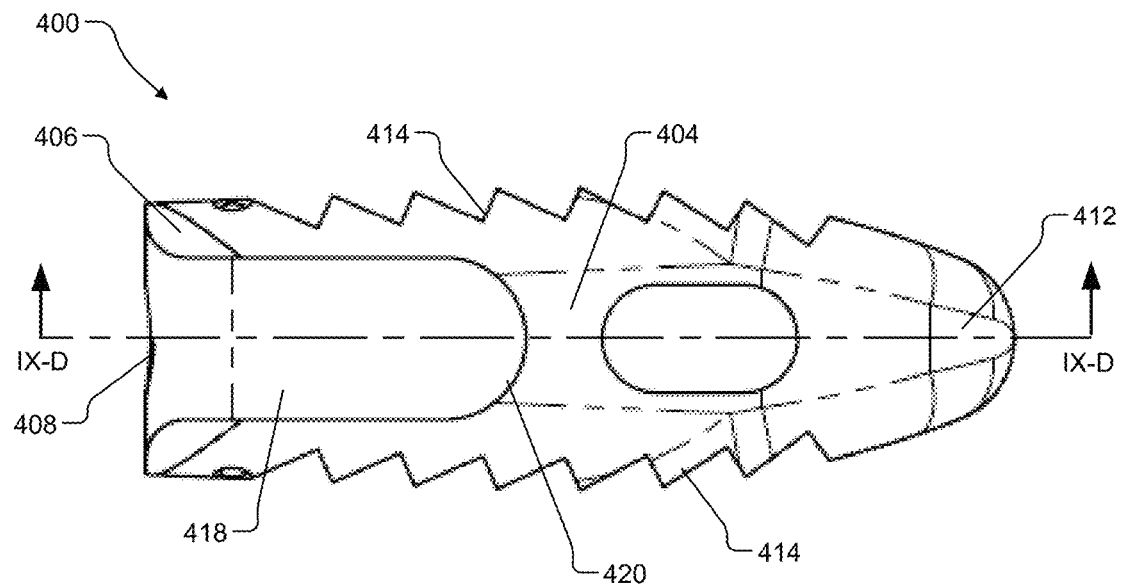
FIG. 9C is a side view of the exemplary implant and FIG. 9D is a cross-sectional view looking into the plane IX-D.
Figure 9D:
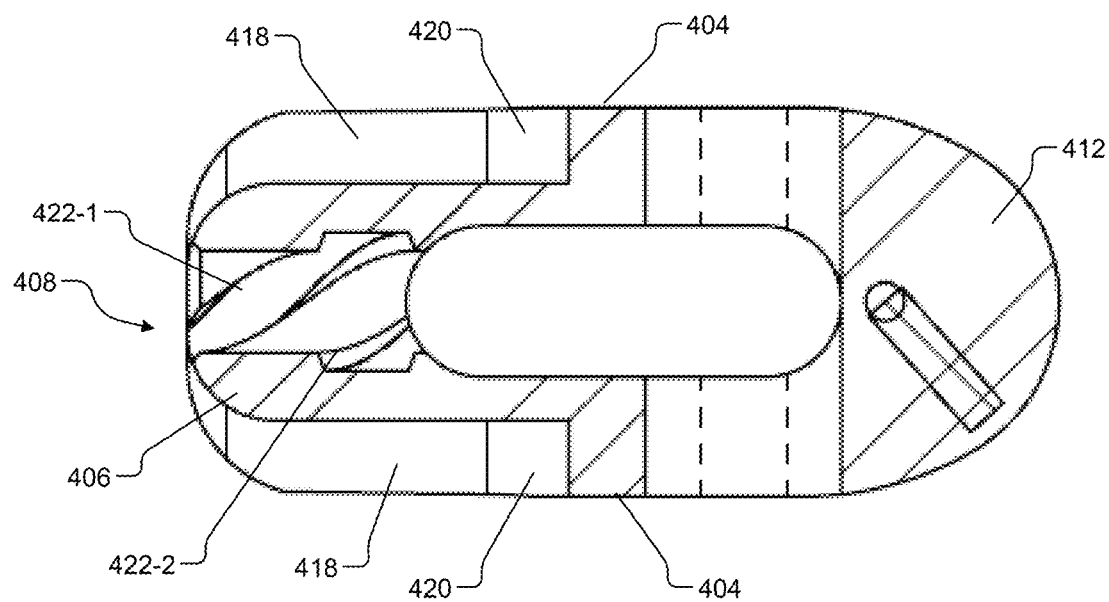
Figure 9E:
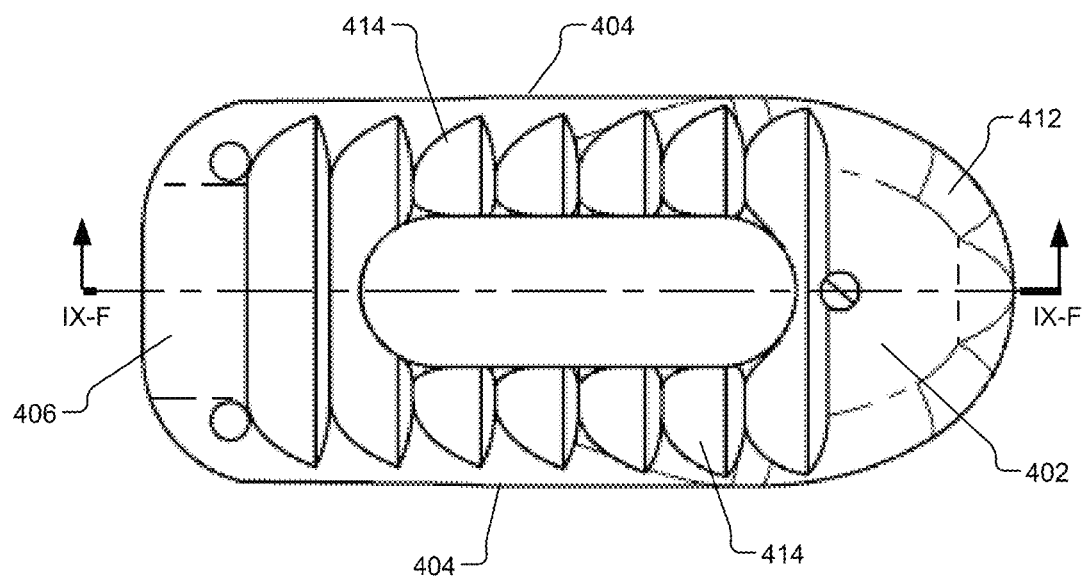
FIG. 9E is a top view of the exemplary implant and FIG. 9F is a cross-sectional view looking into the plane IX-F.
Figure 9F:
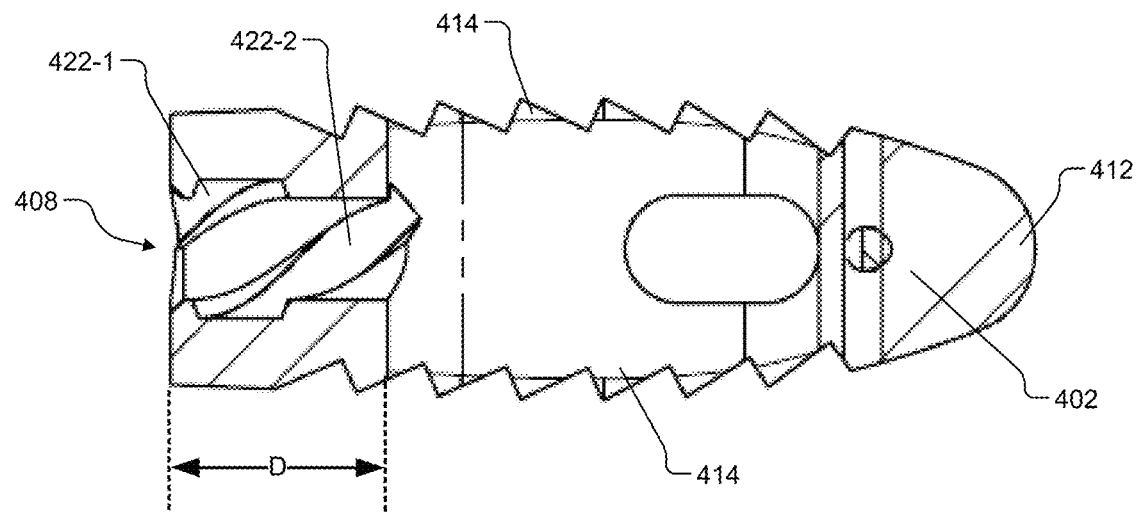
Figure 9G:
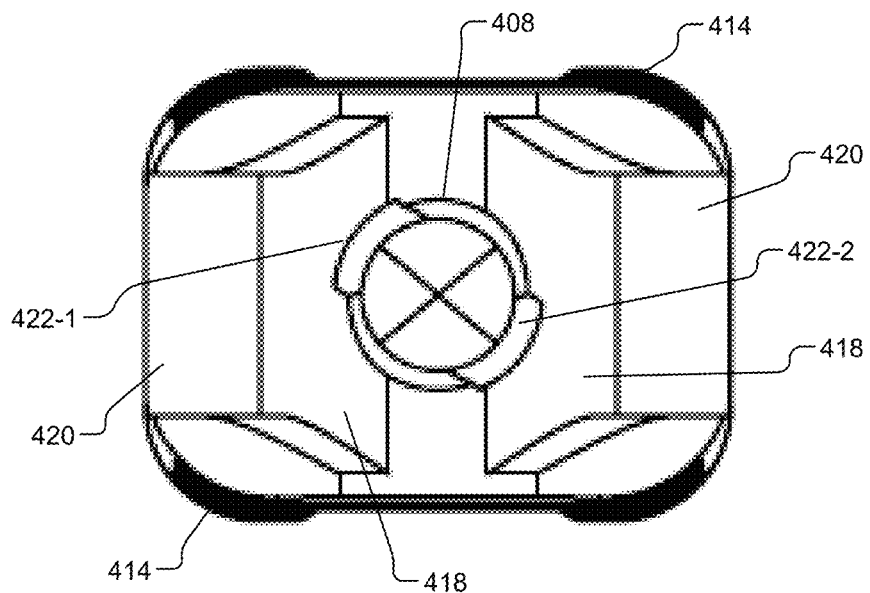
FIG. 9G is a posterior view of the exemplary implant illustrating a dual lead thread according to the principles of the present disclosure.
Figure 10:
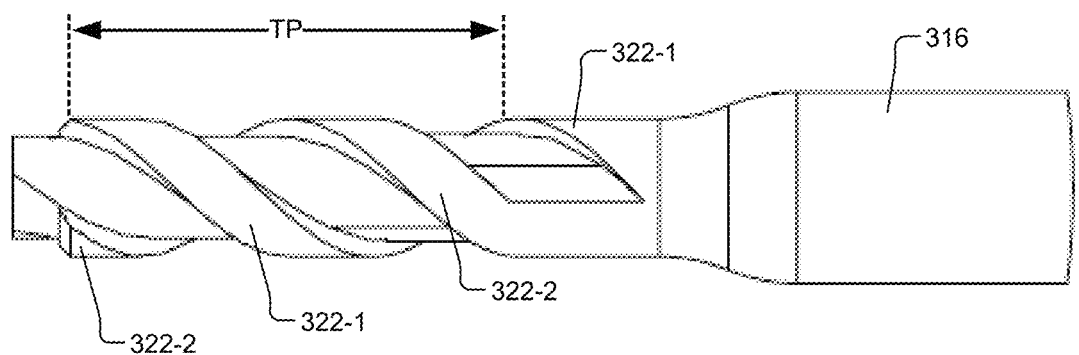
FIG. 10 is a partial side view of the distal end of the inner member of the inserter according to the principles of the present disclosure.

Referring now to FIGS. 9A-9B, perspective views of the exemplary spinal implant 400 are shown. The spinal implant 400 may include a bullet nose 412 at the distal end 202 for insertion into the intervertebral disc space. A plurality of teeth 414 on superior and inferior surfaces of the middle section 404 may be provided for engagement with endplates of adjacent vertebrae. The spinal implant 400 may form a generally rectangular shape and may include a hollow center 416 to receive fusion promoting materials such as bone graft and the like. Recessed portions 418 on opposite sides of an aperture 420 in the proximal end 406 may be configured to engage with the attachment features 318 of the outer member 308. The aperture 420 at the proximal end 406 may be configured to receive the coupling feature 320 of the inner member 310. The aperture 420 may include a mating feature to couple with the coupling feature 320.

The aperture 408 may include the internal thread 422 corresponding to the thread 322 of the inner member 310. The thread 422 may include a thread pitch TP that is greater than the depth D of the threaded aperture 408 of the proximal end 406 of the spinal implant 400. The thread 408 permits secure coupling of the spinal implant 400 with the inserter 300 by one half rotation of the inner member 310 to engage less than one full crest of the thread 322 with the thread 422. For example, as shown in FIGS. 6C and 6D, the thread 322 includes approximately one crest C1 to engage with approximately one crest of internal thread 422. Thus, the thread pitch TP is greater than or equal to approximately D. For example, the distance to a second crest C2 (not shown) may be greater than the thickness D. For a dual lead thread including a first thread 422-1 and a second thread 422-2, each of the threads 422 may include a thread pitch TP greater than or equal to approximately one half a thickness D of the proximal end 406 of the spinal implant 400. Thus, the thread pitch TP of a dual lead thread 422 is approximately greater than or equal to D/2.

In some examples, the aperture 420 includes an Acme thread. In some examples, the Acme thread includes a double lead. In some examples, the Acme thread includes a double lead and a substantially steep thread pitch greater than or equal to approximately D/2 where D is a thickness of the proximal end 406 of the spinal implant 400. In some examples, the aperture 408 permits secure coupling of the spinal implant 400 with the inserter 300 by 180 degrees of rotation of the inner member 310. For example, one half-turn of the inner member 310 may cause the coupling feature 320 to be in full coupling engagement the thread 422 in the proximal end 406 of the spinal implant 400. The coupling feature 320 and the spinal implant 400 are in full coupling engagement after one half turn of the handle 326. Full coupling engagement includes engagement of the distal attachment features 318 with the recessed portions 418 sufficient for insertion and positioning of the spinal implant 400. For example, distal ends 372 of the distal attachment features 318 may engage distal ends 420 of the recessed portions 418.

In some examples, the aperture 408 includes thread 422 with an Acme thread. In some examples, the Acme thread includes a substantially steep thread pitch greater than or equal to approximately half a thickness of a sidewall of the proximal end 406 of the spinal implant 400. In some examples, the Acme thread includes a double lead. In some examples, the Acme thread includes a double lead and a substantially steep thread pitch greater than or equal to approximately half a thickness of a sidewall portion of the proximal end 406 of the spinal implant 400. In some examples, the aperture 408 permits secure coupling of the spinal implant 400 with the inserter 300 by 180 degrees of rotation of the inner member 310. For example, one half-turn of the inner member 310 may cause the coupling feature to fully engage thread of the aperture 408 from an outer surface opening to an inner surface opening as described herein.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An instrument for insertion and positioning of a spinal implant, comprising: an outer member having a distal attachment feature configured to engage with the spinal implant, a tubular member, and a proximal housing; an inner member rotatably disposed within a lumen of the outer member and including a distal coupling feature for coupling with a threaded aperture within the spinal implant, an elongated shaft within the tubular member, and a proximal end operably coupled with a handle to rotate the inner member relative to the outer member; and a first thread on the distal coupling feature having a first lead, the first thread including a first thread pitch greater than or equal to one third of a depth of the threaded aperture of the spinal implant; a selector mechanism coupling the proximal end of the inner member with the handle for selectively locking the inner member relative to the outer member, wherein the selector mechanism comprises a selector member received by a first recessed portion in a first configuration, a circumferential channel in communication with the first recessed portions in a second configuration, and a second recessed portion in communication with the circumferential channel in a third configuration.

2. The instrument of claim 1, wherein the thread pitch is greater than or equal to the depth of the threaded aperture of the spinal implant.

3. The instrument of claim 1, wherein the thread pitch is greater than or equal to two times the depth of the threaded aperture of the spinal implant.

4. The instrument of claim 1, further comprising a second thread with a second lead, the second thread including a second thread pitch equal to the first thread pitch.

5. The instrument of claim 1, wherein the first thread comprises a long lead trapezoidal form thread.

6. The instrument of claim 1, wherein one half rotation of the inner member engages less than one full thread of the first thread with the threaded aperture to position the spinal implant into fully coupled engagement with the distal attachment feature.

7. The instrument of claim 6, wherein the distal attachment feature comprises a pair of attachment features extending distally in a fork formation around the coupling feature to engage with a pair of recessed portions of the spinal implant.

8. The instrument of claim 1, in combination with the spinal implant, the spinal implant further comprising: a distal end for insertion; a middle section including a pair of recessed portions on an outer surface of the middle section; and a proximal end including the threaded aperture with a thread pitch corresponding to the first thread pitch.

9. The instrument of claim 1, wherein when the selector mechanism is in one of the first and the third configurations, the inner member is locked relative to the outer member.

10. The instrument of claim 1, wherein when the selector mechanism is in the second configuration, the inner member freely rotates 180 degrees relative to the outer member to secure the spinal implant to the coupling feature and fully engage the distal attachment features with recessed portions of the spinal implant.

11. An instrument for insertion and positioning of a spinal implant, comprising: an outer member including: a tubular member having a lumen extending along a longitudinal axis of the tubular member, a pair of distal attachment features comprising one of tangs, prongs, and projections that extend distally from the tubular member and are configured to engage with recessed portions of the spinal implant, and a proximal housing comprising a proximal facing portion with a first recessed portion, a second recessed portion, and a channel communicating between the first and second recessed portions; an inner member rotatably disposed within the lumen including: a distal coupling feature comprising a dual long-lead trapezoidal form thread with a thread pitch greater than a depth of an aperture of the spinal implant, an elongate shaft within the lumen configured to rotate the distal coupling feature, and a proximal end operably coupled with a handle that rotates the inner member relative to the outer member; and a selector mechanism operably coupling the proximal end of the inner member with the handle and including a selector member with a tab, wherein the tab is positioned within the first recessed portion to prevent rotation of the inner member relative to the outer member in a first configuration, wherein the tab is positioned within the channel while the inner member rotates relative to the outer member to couple the distal coupling feature with the aperture of the spinal implant in a second configuration, and wherein the tab is positioned within the second recessed portion to prevent rotation of the inner member relative to the outer member after coupling the spinal implant in a third configuration.

12. The instrument of claim 11, in combination with the spinal implant, wherein the proximal end of the spinal implant includes an aperture with a mating dual lead Acme thread corresponding to the thread of the distal coupling feature, and wherein the pair of recessed portions are disposed on opposite sides of the aperture and extending towards a middle section of the spinal implant.

13. The instrument of claim 11, wherein the coupling feature and the spinal implant are in full coupling engagement after one half turn of the handle, wherein full coupling engagement includes engagement of the distal attachment features with the recessed portions sufficient for insertion and positioning of the spinal implant.

14. A system for promoting fusion between adjacent vertebrae, comprising: a spinal implant including a distal end, a middle section, and a proximal end, an aperture in the proximal end with a dual long-lead trapezoidal form thread, and a pair of recessed portions disposed on opposite sides of the aperture and extending along an outer surface the middle section; an instrument for insertion and positioning of the spinal implant including an outer member including a tubular member with a lumen extending along a longitudinal axis of the tubular member, a pair of distal attachment features extending distally from the tubular member and configured to engage with the pair of recessed portions, and a proximal housing; an inner member rotatably disposed within the lumen and including a distal coupling feature with a mating dual long-lead trapezoidal form thread, an elongated shaft within the lumen configured to rotate the distal coupling feature to couple with the aperture, and a proximal end operably coupled with a handle that rotates the inner member relative to the outer member, a selector mechanism operably coupling the proximal end of the inner member with the handle and including a selector member with a tab, wherein the tab is positioned within the first recessed portion to prevent rotation of the inner member relative to the outer member in a first configuration, wherein the tab is positioned within the channel while the inner member rotates relative to the outer member to couple the distal coupling feature with the proximal end of the spinal implant in a second configuration, and wherein the tab is positioned within the second recessed portion to prevent rotation of the inner member relative to the outer member after coupling the spinal implant in a third configuration.

15. The system of claim 14, wherein the proximal housing further comprises a proximal facing portion with a first recessed portion, a second recessed portion, and a channel communicating between the first and second recessed portions.

16. The instrument of claim 15, wherein the first recessed portion and the second recessed portion are arranged at 180 degrees about the proximal facing portion of the proximal housing, wherein the open channel comprises a circumferential channel extending 180 degrees about the proximal facing portion of the proximal housing.

17. The instrument of claim 16, wherein the coupling feature and the spinal implant are in full coupling engagement after one half turn of the handle, wherein full coupling engagement includes engagement of the distal attachment features with the recessed portions sufficient for insertion and positioning of the spinal implant.

* * * * *